US008835397B2

(12) United States Patent
Nanjan et al.

(10) Patent No.: US 8,835,397 B2
(45) Date of Patent: Sep. 16, 2014

(54) MACROCYCLIC LACTONE TABLET FORMULATION

(75) Inventors: Karthigeyan Nanjan, Auckland (NZ); Fadil Al Alawi, Auckland (NZ); Wayne Frederick Leech, Auckland (NZ); Man Yik Li, Chai Wan (HK); Steve Li, Chai Wan (HK)

(73) Assignee: Bayer New Zealand Ltd., Hamilton (NZ)

( * ) Notice: Subject to any disclaimer, the term of this patent is extended or adjusted under 35 U.S.C. 154(b) by 163 days.

(21) Appl. No.: 12/520,269

(22) PCT Filed: Dec. 18, 2007

(86) PCT No.: PCT/NZ2007/000371
§ 371 (c)(1),
(2), (4) Date: Sep. 11, 2009

(87) PCT Pub. No.: WO2008/075979
PCT Pub. Date: Jun. 26, 2008

(65) Prior Publication Data
US 2010/0016248 A1    Jan. 21, 2010

(30) Foreign Application Priority Data
Dec. 21, 2006  (NZ) ........................................ 552290

(51) Int. Cl.
*A61K 31/70*    (2006.01)
*A61K 9/20*    (2006.01)

(52) U.S. Cl.
CPC .............. *A61K 9/2018* (2013.01); *A61K 9/2009* (2013.01); *A61K 9/2027* (2013.01); *A61K 9/2059* (2013.01); *A61K 9/2013* (2013.01)
USPC ........................................... 514/30; 424/408

(58) Field of Classification Search
USPC .......................................................... 514/30
See application file for complete search history.

(56) References Cited

U.S. PATENT DOCUMENTS

| 4,389,397 | A  | * | 6/1983 | Lo et al. .......................... 514/53 |
| 5,045,082 | A  | * | 9/1991 | Ayer et al. .................. 604/892.1 |
| 7,407,667 | B2 | * | 8/2008 | Zerrer et al. .................. 424/405 |
| 2004/0151759 | A1 | | 8/2004 | Cleverly et al. |
| 2005/0032719 | A1 | | 2/2005 | Cottrell et al. |
| 2005/0203034 | A1 | | 9/2005 | Ahn et al. |

FOREIGN PATENT DOCUMENTS

| WO | WO 03/002102 A1 | 1/2003 |
| WO | WO 03/009833 A1 | 2/2003 |
| WO | WO 03/011214 A2 | 2/2003 |
| WO | WO 2004/016252 A1 | 2/2004 |
| WO | WO 2006/036625 | 9/2005 |

OTHER PUBLICATIONS

International Search Report prepared by the Australian Patent Office on Jun. 2, 2008, for International Application No. PCT/NZ2007/000371.
Written Opinion prepared by the Australian Patent Office on Jun. 2, 2008, for International Application No. PCT/NZ2007/000371.
International Preliminary Report on Patentability prepared by the Australian Patent Office on Jun. 2, 2008, for International Application No. PCT/NZ2007/000371.

* cited by examiner

*Primary Examiner* — Elli Peselev (57) ABSTRACT

The invention relates to a table formulated for administration to an animal to treat parasite infestation. The tablet includes at least one macrocyclic lactone compound with anthelmintic activity dissolved in at least one organic solvent and subsequently formulated into a tablet. The tablets produced have a high degree of stability when stored over time and also provide the animal with a dose of agent sufficient to be therapeutically effective.

31 Claims, 2 Drawing Sheets

MACROCYCLIC LACTONE TABLET FORMULATION

CROSS REFERENCE TO RELATED APPLIACTIONS

This application is a national stage application under 35 U.S.C. 371 of PCT Application No. PCT/NZ2007/000371 having an international filing date of 18 Dec. 2007, which designated the United States, which PCT application claimed the benefit of New Zealand Patent Application No. 552290 filed 21 Dec. 2006, the entire disclosure of each of which are incorporated herein by reference.

TECHNICAL FIELD

The invention relates to a tablet formulation. More specifically, the invention relates to a tablet formulation containing at least one lipophilic compound with anthelmintic activity for use in treatment of an animal.

BACKGROUND ART

Anthelmintic chemical compounds are widely known agents that are destructive to worms and used for treating internal and external parasitic infestations in animals including humans.

There are many different types of anthelmintic compound, each with varying degrees of parasitic activity and chemical properties.

A difficulty in formulating such compounds is that many are extremely insoluble in aqueous environments such as extracellular fluids thus they need to be formulated to ensure they are bioavailable. In addition, in order to make these compounds soluble, different conditions may be required resulting in situations where one compound may be solubilized by for example, by reducing pH. This change can cause other compounds in the formulation to become insoluble, or the change may cause physical or chemical degradation of another compound in the formulation. In addition, the change may cause adverse side effects in the animal.

Stabilising and providing combinations of anthelmintic agents for oral administration have been considered in the prior art. A wide variety of advantages may be obtained by such combinations and these are discussed in prior art patent specifications including WO 00/74489 and WO 02/09764, incorporated herein by reference.

In the present invention, an aim is to provide a tablet formulation containing at least one lipophilic compound that has anthelmintic activity that presents the active in a bioavailable form.

The macrocyclic lactone family of anthelmintic compounds, which family includes abamectin and ivermectin, present a difficult challenge in formulation as such compounds are largely insoluble in aqueous environments such as in an animal's body. An important factor is to ensure that the tablet dissolves on administration and releases the active agent or agents in a form that is bioavailable and does not simply pass through the animal without achieving the desired therapeutic effect.

One attempt to address the above problem is an ivermectin capsule for the treatment of internal and external parasites in adult sheep and lambs (marketed in New Zealand as IVOMEC® MAXIMIZER™ CR). This product is formulated to provide a slow release of ivermectin to 'control' parasites over a time period of 100 days. A disadvantage of this product is the continuous release of ivermectin at levels below that required to kill adult parasites. The drug levels are designed to the kill incoming larvae, which require a lower dose rate for control than adult parasites. Besides not addressing adult parasites, use of the product may lead to drug resistance where the low dose allows adult parasites to become resistant to the ivermectin. Further reinforcing the resistance problem is that, when this product is given to adult ewes, drug resistant parasites may also be transferred to progeny from the ewes prolonging resistance across different generations. A further problem with the above slow release capsule is that the time period between delivery and slaughter must be sufficiently long to ensure all agent has been released. By contrast, fast release products are more flexible as the time period between delivery and slaughter may be significantly shorter.

It should be appreciated that it is desirable to have a formulation:
- for delivery of parasiticidal compounds including lipophilic agents,
- which stabilises these agents so that they may be stored over time with minimal physical or chemical degradation, and,
- delivers a consistent dose of the agents on administration to an animal.

It is an object of the present invention to address the foregoing problems or at least to provide the public with a useful choice.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process. Further aspects and advantages of the present invention will become apparent from the ensuing description which is given by way of example only.

DISCLOSURE OF INVENTION

According to one aspect of the present invention there is provided a tablet formulated for administration to an animal characterised in that the tablet includes at least one solubilisable lipophilic compound having anthelmintic activity.

For the purposes of this specification, the term 'tablet' refers to the formulation being administered orally and in a consistency able to be administered as a granular material, discrete tablet or capsule, or alternatively expelled by device such as a 'pill popper', stomach tube or other delivery device.

Preferably, at least one of the anthelmintic compounds used in the tablet may be characterised by being lipophilic and having poor solubility and/or poor dispersion characteristics in an aqueous environment. It is understood by the inventors that this poor solubility and/or poor dispersion may result in corresponding poor oral absorption, which may lead to poor pharmacokinetics. These factors may contribute to the compound having poor oral bioavailability. If such a compound is administered absent of a suitably formulated delivery system, the compound may either not be absorbed or be only poorly absorbed within an aqueous environment such as the blood stream.

Preferably a compound may display 'poor oral bioavailability' if, when orally delivered to an animal on its own (i.e. absent of a suitably formulated delivery system), it achieves less than approximately 20% absorption of the compound into the blood stream when compared with the results obtained using an equivalent single active oral drench.

Preferably, an 'aqueous environment' may be extracellular fluid.

Preferably, the solubilisable lipophilic active compound is a macrocyclic lactone. Preferably, the solubilisable lipophilic anthelmintic compound is abamectin or ivermectin. More preferably, the solubilisable lipophilic anthelmintic compound is abamectin, although it should be appreciated that as ivermectin also has similar physical properties to abamectin, ivermectin is also encompassed within the present invention.

Preferably, the solubilisable lipophilic compound or compounds included in the tablet are at a dose sufficient to: prevent growth of parasites; reduce parasite numbers; kill parasites; kill incoming parasite larvae; lower the number of surviving incoming parasite larvae; kill or reduce the number of hypobiotic state parasites; and combinations thereof.

In a preferred embodiment, the tablet includes sufficient solubilisable lipophilic compound or compounds to provide the animal with a dose of the compound or compounds equivalent to that which would be obtained from an oral drench containing the same solubilisable lipophilic compound or compounds.

Preferably, where abamectin is present, the abamectin is included at a dose rate of at least approximately 0.2 mg to 0.6 mg of abamectin per kg of animal body weight. More preferably, the dose rate is approximately 0.2 mg/kg. Most preferably the dose rate is approximately 0.4 mg/kg.

It should be appreciated that this dose is sufficient to kill or at least reduce parasite infestation including both larvae and adult parasites.

In one embodiment of the present invention, the amount of active ingredient per tablet for a cattle formulation is 64 mg abamectin per tablet dosed to an animal weighing approximately 160 kg. It is the inventor's experience that this level of abamectin provides a blood level of abamectin to the animal equivalent to that which would be obtained from an oral drench containing abamectin such as the product GENESIS™. It should be appreciated that the dosage of abamectin may be varied depending on the amount of abamectin desired to be administered and that levels of abamectin above or below 64 mg may be used without departing from the scope of the invention. Similarly, the dose may be varied for different animals.

Further, those skilled in the art should also appreciate that the present invention provides a pulse, fast release action with a similar concentration profile over time as the GENESIS™ oral drench product.

In an alternative embodiment, the solubilisable lipophilic compound is ivermectin included at a rate of 0.2 mg to 0.6 mg of ivermectin per kg of animal weight.

Preferably, the solubilisable lipophilic compound is formulated to be rapidly released on oral administration.

Preferably, the solubilisable lipophilic compound is formulated so that the compound or compounds remain present in the bloodstream of the animal for at least 24 hours.

Preferably, the solubilisable lipophilic compound is formulated so that the compound or compounds dissipate from the bloodstream of the animal in a similar manner as an oral drench. It is understood by the applicant that the compound has left the blood stream after a time period of no more than two weeks.

In one embodiment, the solubilisable lipophilic compound is dissolved in at least one organic solvent and subsequently mixed with at least one second organic solvent (termed a 'co-solvent' for the purposes of this specification). Preferably, the solvent or solvents and co-solvent or co-solvents are different compounds. In an alternative embodiment, the solubilisable lipophilic compound is dissolved in at least one first organic solvent or solvents and no co-solvent is used.

Preferably, the first organic solvent or solvents may be selected from: an alcohol, a glycol, an ether, a pyrrolidone compound with two or more carbon atoms, and combinations thereof. More preferably, the solvent or solvents may include: ethyl alcohol, benzyl alcohol, phenethyl alcohol, ethyl benzyl alcohol and other aromatic monohydric alcohols; glycols, glycol ethers, glycol ether acetates, $C_1$ to $C_8$ alkyl pyrrolidones, and combinations thereof. In a preferred embodiment, the solvent is benzyl alcohol which is preferred as it not only dissolves the lipophilic compound, but also, acting with the co-solvent, stabilises the compound increasing the overall stability of the product.

Preferably, the co-solvent or co-solvents are alcohol or ether compounds with three or more carbon atoms. More preferably, the co-solvent or co-solvents include: diol alcohols or ethers including glycols, aromatic monohydric alcohols, glycol ethers, glycol ether acetates, and combinations thereof. In a preferred embodiment, the co-solvent is a propylene glycol compound such as monopropylene glycol which is preferred as it not only mixes with the lipophilic compound and solvent but also stabilises the compound increasing stability and provides emulsifying properties. It is understood that the emulsifying properties assist in preventing crystallisation/precipitation of the lipophilic compound on release in the gut although other factors may also account for the increased bioavailability effect and this description should not be seen as limiting.

A further advantage of the organic solvents and co-solvents chosen are that they provide improved bioavailability by the solvents giving a transmucosal effect whereby the solvents and co-solvents assist in transfer of the agent or agents from the gut and into the animal bloodstream.

Without use of the above solvents and co-solvents, the solubilisable lipophilic compound or compounds would pass straight through the animal on administration with no or only sparing absorption. By dissolution and mixing with solvents and co-solvents, the solubilisable lipophilic anthelmintic compound is made absorbable.

In addition to increasing oral bioavailability, the inventors have found that the resulting tablet formulation remains stable with minimal loss of the active ingredient during storage. For the purposes of this specification, the term 'stable' refers to at least 6 months (preferably 18 months) chemical stability (e.g. within ±10% w/w active agent of the stated composition) of active agent when stored at 40° C. or below and at a high humidity (relative humidity of less than 75%) and of a reasonable physical stability such that no physical alteration is observed in the tablet during storage or at the time of administration.

Other agents are also envisaged as being added to the formulation including other anthelmintic agents as well as other non-anthelmintic agents. For example, in farming applications, other nutrients such as trace minerals may be added to the formulation to allow the animal to be dosed for parasites but also to enhance the animal's nutrition.

In one embodiment mineral supplementation may be included in the formulation to provide a source of cobalt, copper, iodine, selenium and zinc.

In a further embodiment additional inert compositions are added to the tablet including: binders, fillers, bulking agents, carriers, disintegration agents, glidants, lubricants, and combinations thereof.

In preferred embodiments, the tablet disintegrates within approximately 15 minutes when placed in water at 37° C.

According to a further aspect of the present invention there is provided a tablet formulated for administration to an animal characterised in that the tablet includes abamectin, an organic solvent and an organic co-solvent.

Preferably, the tablet as described above includes the above components in a ratio within the range of approximately 1 part abamectin to 0.8-1.2 parts organic solvent to 3.2-3.6 parts organic co-solvent.

According to a further aspect of the present invention there is provided a tablet formulated for administration to an animal characterised in that the tablet includes: a macrocyclic lactone, benzyl alcohol and a propylene glycol compound.

Preferably, the tablet as described above includes the above components in a ratio within the range of approximately 1 part macrocyclic lactone to 0.8-1.2 parts benzyl alcohol to 3.2-3.6 parts propylene glycol compound.

According to a further aspect of the present invention there is provided a method of treating non-human animals for parasite infestation by administration of a tablet composition containing at least one solubilisable lipophilic anthelmintic compound substantially as described above.

According to a further aspect of the present invention there is provided the use of a tablet composition containing at least one solubilisable lipophilic anthelmintic compound substantially as described above in the treatment of a parasite infestation in non-human animals.

Preferably, the non-human animal is a ruminant animal. In specific embodiments envisaged by the inventors, the animals are ovine and bovine species although it is anticipated that any animal susceptible to parasite infestation treatable using an anthelmintic composition may be treated.

Preferably, the parasites treated include endoparasites.

According to a further aspect of the present invention there is provided a kit containing a pill administration device and a package of tablets substantially as described above.

It should be appreciated that the tablet may be sold commercially in bulk or in smaller kits. Smaller kits containing a package of tablets have the advantage over existing drenches and pour on formulations in that large amounts of formulation need not be purchased. It should be noted that, due to the stability of the tablets of the present invention, the packaging need not provide specific stabilising properties but rather is likely to be best used to assist in administration such as by use of labelling to identify sequence or dose information. Commercially sold drenches and pour on formulations are typically sold in containers including 500 or more doses which is excessive for the small lifestyle farmer or other purchasers. The convenience of a package also lends itself well to smaller dosing runs with little mess and fuss required.

In one embodiment the package may be sold with a disposable tablet applicator in order to further simplify the process for the user. Applicator devices such as a pill popper or gas actuated applicator may also be included. In a further embodiment, the applicator may be replaced by an administration/swallowing-enhancing coating such as a dough in which the tablet is encased and which masks the tablet from the animal.

As should be appreciated by those skilled in the art, a key advantage from the formulation is that lipophilic or sparingly soluble agents are formulated as a tablet to increase the oral bioavailability of such agents and allow the agent(s) to be absorbed into an animal on administration.

A further advantage of the present invention is that tablets may be advantageous in small farm applications. At present drenches and topical pour-on solutions are packaged in large containers for use in dosing large numbers of animals (typically 500 doses). The cost of these treatments is considerable. In contrast, the present invention may be sold as a package containing any number of doses which, for a small farm of lifestyle block would be preferable than purchasing a large container at significant cost. Purchase of a small number of tablets would also remove the need to dump unused drenches or pour-on solutions that have passed their expiry date.

BRIEF DESCRIPTION OF DRAWINGS

Further aspects of the present invention will become apparent from the ensuing description which is given by way of example only and with reference to the accompanying drawings in which.

BEST MODES FOR CARRYING OUT THE INVENTION

Examples are now provided showing various embodiments of the present invention.

Example 1

In a first trial, the inventors developed tablet formulations containing abamectin and the bioavailability of these formulations was tested.

Formulations

Three formulations were tested:

Reformulation 1 includes:

TABLE 1

Reformulation 1 Composition

| Component | Quantity per tablet [%] | Quantity per tablet (mg) |
|---|---|---|
| Abamectin | 1.35 | 12.0 |
| Monopropylene glycol | 12.13 | 108.0 |
| Levamisole hydrochloride | 51.45 | 457.9 |
| Albendazole | 25.63 | 228.1 |
| Polyvinyl Pyrrolidone | 0.26 | 2.35 |
| Corn starch | 3.24 | 28.86 |

TABLE 1-continued

Reformulation 1 Composition

| Component | Quantity per tablet [%] | Quantity per tablet (mg) |
| --- | --- | --- |
| Sodium starch glycolate | 3.95 | 35.19 |
| Aerosil 200 | 0.88 | 7.82 |
| Magnesium stearate | 1.10 | 9.78 |
| Total: | 100% | 890 mg |

Reformulation 2 includes:

TABLE 2

Reformulation 2 Composition

| Component | Quantity per tablet [%] | Quantity per tablet (mg) |
| --- | --- | --- |
| Abamectin | 1.43 | 12.0 |
| Monopropylene glycol | 5.14 | 43.0 |
| Benzyl alcohol | 1.43 | 12.0 |
| Levamisole hydrochloride | 54.71 | 457.9 |
| Albendazole | 27.25 | 228.1 |
| Polyvinyl Pyrrolidone | 0.28 | 2.35 |
| Corn starch | 3.45 | 28.86 |
| Sodium starch glycolate | 4.20 | 35.19 |
| Aerosil 200 | 0.93 | 7.82 |
| Magnesium stearate | 1.17 | 9.78 |
| Total: | 100% | 837 mg |

Reformulation 3 includes:

TABLE 3

Reformulation 3 Composition

| Component | Quantity per tablet [%] | Quantity per tablet (mg) |
| --- | --- | --- |
| Abamectin | 1.35 | 12.0 |
| Monopropylene glycol | 6.52 | 58.0 |
| Sodium Lauryl Sulphate | 5.62 | 50.0 |
| Levamisole hydrochloride | 51.45 | 457.9 |
| Albendazole | 25.63 | 228.1 |
| Polyvinyl Pyrrolidone | 0.26 | 2.35 |
| Corn starch | 3.24 | 28.86 |
| Sodium starch glycolate | 3.95 | 35.19 |
| Aerosil 200 | 0.88 | 7.82 |
| Magnesium stearate | 1.10 | 9.78 |
| Total: | 100% | 890 mg |

Reformulation 1 and Reformulation 2 were investigated during the first treatment session. In the second treatment session, Reformulation 3 and the Reference products were compared. The animals were then re-randomised for the third sampling session, in which Reformulation 2 was compared with the Reference products.

Animal Selection

Twelve sheep weighing 62.5 kg to 78 kg (mean=68.6 kg) were all dosed to individual liveweight with one anthelmintic treatment, at the standard dose rate of 0.2 mg/kg for abamectin.

Prior to administration of the invention or Reference formulation, all animals were dosed to their individual liveweight with SCANDA™ (Batch 52888, expiry April 2006) at least 14 days prior to each treatment session, and tested free of strongylid nematodes (via faecal egg count) prior to the commencement of each treatment session.

Dosing

All sheep were administered with a dose sufficient for a 60 kg animal.

Reference Products

The Reference product used was the single anthelmintic abamectin drench GENESIS™ Oral Drench (Batch 2204, Expiry February /2009).

It should be appreciated that this reference product provides a high bar in terms of bioavailability to be reached by the present invention. Therefore, providing a tablet formulation where comparable levels of bioavailability are achieved as a single oral drench would be an advantage. It should be noted that lower levels of oral bioavailability may still be of commercial value given the advantages offered from tablet administration noted previously.

Sampling Times

Blood samples (4 ml per sample) were taken from the tested animals at time intervals of 6 hours (h), 12 h, and 24 h post administration.

Blood was collected from the jugular vein via venipuncture, directly into heparinised vacutainer tubes and refrigerated at 4° C. until processing. It was then centrifuged at 2500 rpm for 10 minutes before the plasma was collected, and divided into test (2 ml/analyte) and reserve (2 ml), samples and frozen. Test and reserve samples were maintained at −18° C. in separate freezers before laboratory analysis.

Results

Treatment Session 1

Abamectin

Figure 1:
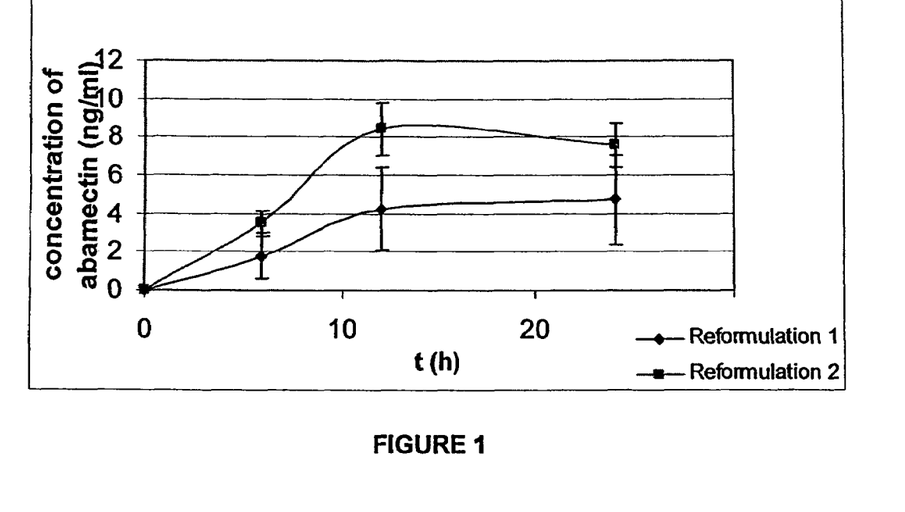
FIG. 1 shows a graph of abamectin blood levels measured post administration based on two formulations labelled Reformulation 1 and Reformulation 2.

Blood plasma levels for abamectin peaked at 4.7 ng/ml and 8.5 ng/ml for Reformulation 1 and Reformulation 2 respectively (FIG. 1). The $T_{max}$ occurred 24 h and 12 h for the two formulations, indicating the absorption of abamectin from Reformulation 1 was delayed.

Treatment Session 2

Abamectin

Figure 2:
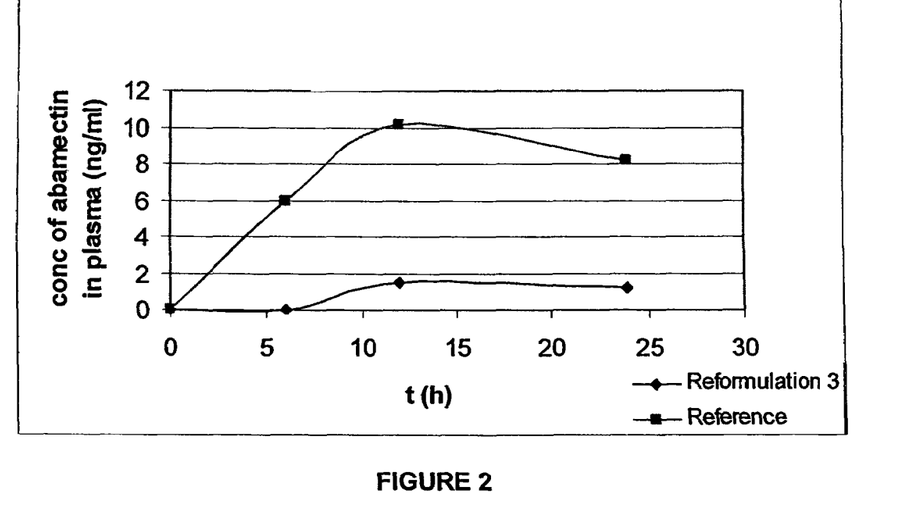
FIG. 2 shows a graph of abamectin blood levels measured post administration based on a third formulation labelled Reformulation 3 and a Reference abamectin oral drench product.

The abamectin plasma profiles observed for Reformulation 3 and the Reference product are shown (FIG. 2). The $C_{max}$ observed for the Reformulation 3 and Reference treatment groups were 1.5 ng/ml and 10.2 ng/ml respectively.

In this case, abamectin absorbed from Reformulation 3 was not comparable to levels observed from the Reference oral drench GENESIS™.

Treatment Session 3

After comparing the Reformulation 2 results from Treatment Session 1 with the Reference results from Treatment Session 2, it was decided to compare Reformulation 2 with the Reference products in the third Treatment Session (Treatment Session 3). This was done as a side by side trial to re-confirm the results observed in Treatment Sessions 1 and 2.

Abamectin

Figure 3:
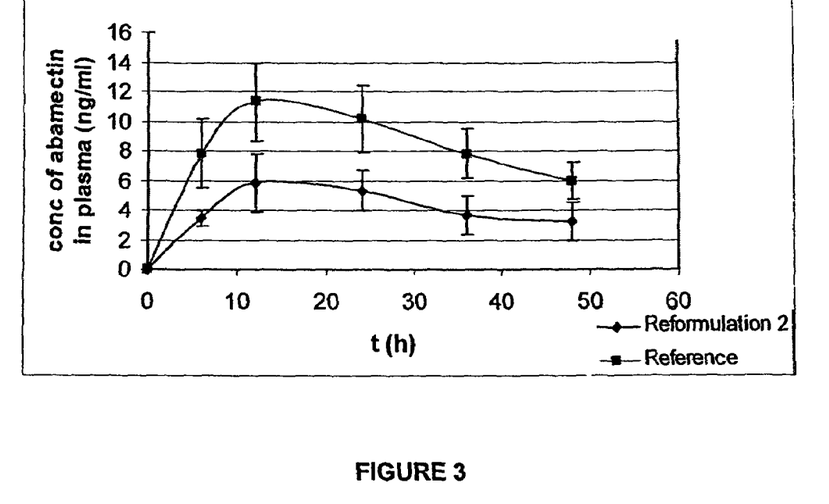
FIG. 3 shows a graph of abamectin blood levels measured post administration based on Reformulation 2 and a Reference abamectin oral drench product.

The abamectin plasma profiles observed for Reformulation 2 and the Reference product are shown (FIG. 3). The $C_{max}$ observed for the Reformulation 2 and Reference treatment groups were 5.8 ng/ml and 11.3 ng/ml respectively. The $T_{max}$ for both formulations occurred 12 h post administration. Whilst some effect was achieved using Reformulation 2, the bioavailability of abamectin from Reformulation 2 approximates half that of the Reference product GENESIS™.

Example 2

Given the results in Example 1, a further trial was completed to determine the influence of the formulation on the degree of absorption of abamectin. This was completed by ascertaining baseline levels of abamectin drug bioavailability when animals are dosed with raw active (no excipients).

Experimental Design

Five sheep weighing 59.0 kg to 63.5 kg (mean=61.2 kg) were all dosed with one abamectin treatment, which contained a dose sufficient for a 60 kg animal at the standard dose rate of 0.2 mg/kg for abamectin. The abamectin dose was contained within a gelatine capsule.

Experimental Animals

Prior to administration of the invention or Reference formulation, all animals were dosed to their individual liveweight with SCANDA™ (Batch 52888, expiry April 2006) at least 14 days prior to each treatment session, and tested free of strongylid nematodes (via faecal egg count) prior to the commencement of each treatment session.

Dosing Regime

Gelatine capsules containing an abamectin drug (one capsule per sheep) were used. All animals were dosed orally with the assistance of a "pill popper", which was followed immediately by approx 60 ml of tap water. The capsules were dark green in colour, to prevent the light sensitive abamectin from being prematurely exposed to light.

Sampling Times

All animals were blood sampled seven times. Four milliliters of whole blood were collected from each sheep, for each active at each sampling time, and an additional 4 ml reserve sample was collected from each sheep at each sampling time.

Sampling times were 6 h, 12 h, and 24 h post administration.

The blood was collected from the jugular vein via venipuncture, directly into heparinised vacutainer tubes and refrigerated at 4° C. until processing. It was then centrifuged at 2500 rpm for 10 minutes before the plasma was collected, and divided into test (2 ml/analyte) and reserve (2 ml), samples and frozen. Test and reserve samples were maintained at −18° C. in separate freezers before laboratory analysis.

Results

Abamectin

Blood plasma levels for abamectin peaked just above the detection threshold indicating that abamectin was not absorbed.

The minimal levels of abamectin are not surprising considering that this drug is lipophilic and usually formulated as a solution. Therefore, it is expected to require excipients to facilitate bioavailability of this drug.

Conclusions

The results from this study (when compared to Reference product) suggest that the inclusion of excipients in anthelmintic formulations improves the bioavailability of at least abamectin. In the absence of excipients, plasma levels obtained for abamectin were negligible and lower than that obtained in at least Example 1. The results show that tablet formulations (containing excipients) are an important factor in achieving drug oral bioavailability.

Example 3

A fresh formulation (Reformulation 4) was tested based on prior trials including those identified above in Example 1.

The formulation included:

TABLE 4

Reformulation 4 Composition

| Component | Quantity per tablet [%] | Quantity per tablet (mg) |
|---|---|---|
| Abamectin | 2.12 | 68.0 |
| Monopropylene glycol | 7.17 | 230.0 |
| Benzyl alcohol | 1.99 | 64.0 |
| Levamisole Hydrochloride | 37.38 | 1200.0 |
| Albendazole | 37.38 | 1200.0 |
| Polyvinyl Pyrrolidone | 0.39 | 12.55 |
| Corn starch | 4.80 | 154.07 |
| Sodium starch glycolate | 5.84 | 187.4 |
| Aerosil 200 | 1.30 | 41.76 |
| Magnesium stearate | 1.63 | 52.22 |
| Total: | 100% | 3210 Mg |

The level of abamectin was approximately doubled following the result noted in Example 1 for Reformulation 2.

In this example, the animals used were cattle with other characteristics of the study remaining the same as in Example 1 except that the formulation was altered as noted above.

Results

Abamectin

Abamectin is lipophilic and requires formulation in order for the abamectin to be absorbed. The formulation was altered to increase this absorption by dissolving and mixing the abamectin with solvents. In addition, the dosage of abamectin was approximately doubled in order to achieve a comparable result to the Reference product. Increasing the dose for abamectin is standard practice when designing cattle formulations as sheep have a greater absorption, distribution, metabolism and excretion (ADME) profile than cattle.

Figure 4:
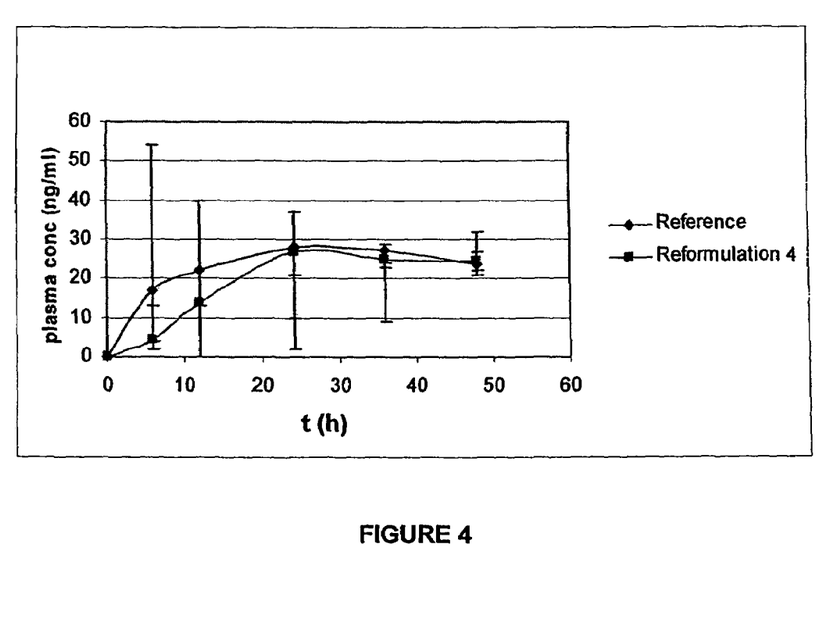
FIG. 4 shows a graph of abamectin blood levels measured post administration of a fourth formulation (Reformulation 4) compared to a Reference abamectin oral drench.

As can be seen in FIG. 4, Reformulation 4 resulted in the abamectin profile becoming almost equivalent with that observed from the Reference oral drench formulation GENESIS™.

Example 4

Two further trials were completed to test the storage stability of the tablets over time. The trials were conducted using Reformulation 2 described above. In the trials, a total of 24 tablets were initially tested for:

General visual description
Disintegration time
Average weight
Weight variation
Concentration of abamectin
Hardness Subsequent to initial tests, a first trial was commenced with 12 tablets placed into an environment held at a constant temperature of 30° C. and 60% relative humidity.

A second trial was also commenced with 12 tablets placed into an environment held at a constant temperature if 40° C. and 75% relative humidity.

The above temperatures and humidity's were chosen as being 'trying' conditions in which the tablets might be stored and represent worst case scenarios where deterioration might occur.

The first trial was conducted over 18 months and the second trial over 6 months. At time intervals noted in Tables 5 and 6 below, the tablets were tested using the same tests as that completed during the initial test and the results compared. Where there were no variations to initial results, the stored tablet was said to 'comply'.

TABLE 5

Storage Stability for a Temperature of 30° C. and Relative Humidity of 60%

| Test | Specification/Standard | Initial | 3 Months | 6 Months | 9 Months | 12 Months | 18 Months |
|---|---|---|---|---|---|---|---|
| Visual Description | An off-white, round, flat tablet: bevelled edge. May have score-line on one side. | Complies | Complies | Complies | Complies | Complies | Complies |
| Disintegration Time in Water | Less than 15 minutes | Complies | Complies | Complies | Complies | Complies | Complies |
| Average tablet weight (mg/tablet) | 795.2-920.8 mg/tablet | Complies | Complies | Complies | Complies | Complies | Complies |
| Weight Variation | Tablets were individually weighed. Of the total tablets, no more than two tablet weights may deviate from the average by more than ±5%. No tablet should deviate by more than 10% | Complies | Complies | Complies | Complies | Complies | Complies |
| Abamectin content | ±10% w/w basis or 10.8-13.20 mg/tablet by HPLC | 12.9 | 12.7 | 11.9 | 11.9 | 12.0 | 12.0 |
| Levamisole HCL content | ±10% w/w basis or 412.2-503.80 mg/tablet by HPLC | 489 | 492 | — | 495 | 486 | 465 |
| Albendazole content | 205.2-250.80 mg/tablet by HPLC | 235 | 247 | 246 | 248 | 244 | 243 |
| Hardness | ≥5.0 Kg | Complies | Complies | Complies | Complies | Complies | Complies |

TABLE 6

Storage Stability for a Temperature of 40° C. and Relative Humidity of 75%

| Test | Specification/Standard | Initial | 1 Month | 3 Months | 6 Months |
|---|---|---|---|---|---|
| Visual Description | An off-white, round, flat tablet: bevelled edge. May have score-line on one side. | Complies | Complies | Complies | Complies |
| Disintegration Time in water | Less than 15 minutes | Complies | Complies | Complies | Complies |
| Average tablet weight (mg/tablet) | 795.2-920.8 mg/tablet | Complies | Complies | Complies | Complies |
| Weight Variation | Tablets were individually weighed. Of the total tablets, no more than two tablet weights may deviate from the average by more than ±5%. No tablet should deviate from the average by more than 10% | Complies | Complies | Complies | Complies |
| Abamectin content | ±10% w/w basis or 10.8-13.20 mg/tablet by HPLC | 12.9 | 12.4 | 12.3 | 11.5 |
| Levamisole HCL content | ±10% w/w basis or 412.2-503.80 mg/tablet by HPLC | 489 | 489 | 473 | 480 |
| Albendazole content | ±10% w/w basis or 205.2-250.80 mg/tablet by HPLC | 235 | 235 | 238 | 243 |
| Hardness | ≥5.0 Kg | Complies | Complies | Complies | Complies |

The above trials showed that the tablet product was remarkably stable and did not breakdown under trying conditions in terms of temperature and humidity over significant time periods.

Example 5

The tablet formulations described above were manufactured as described and packaged in a blister pack sealing the tablets into a package. Markings may be included on the packaging indicating the user when the tablets should be administered and any dosing instructions such as how to use an applicator device such as a pill popper device.

The blister pack is attached to a pill applicator device or composition and placed into a package for sale jointly as a kit.

Besides mechanical devices for administration such as a pill popper or gas actuated applicator, there may be, in the place of an applicator, a dough composition which encases the pill and which masks the pill from the animal. For convenience, a disposable applicator is preferred.

As should be appreciated the kit may contain as little as one dose or many thousands of doses as may be required.

Tablets may be supplied with or without an applicator.

EXAMPLES CONCLUSION

It should be appreciated from the above examples that developing a tablet for delivery of abamectin has presented many challenges. The inventors have achieved this, providing a formulation including abamectin that not only provides agent in a state able to be absorbed but also in a state that may be absorbed at comparable levels to that achieved using other methods of administration, such as oral drenches. The resulting tablet is also stable during storage.

An advantage of tablets is that they provide a fixed and known dose of agent and there is no need to dilute, measure out and use specialised equipment such as drench guns. In addition, tablets may easily be sold in large or small numbers whereas oral drenches for example are only sold in large volumes (and at greater expense).

Aspects of the present invention have been described by way of example only and it should be appreciated that modifications and additions may be made thereto without departing from the scope thereof as defined in the appended claims.

What we claim is:

1. A method of producing a tablet including at least one macrocyclic lactone compound having anthelmintic activity formulated for administration to an animal comprising the steps of
   a) dissolving the at least one macrocyclic lactone compound in at least one organic non-aqueous solvent selected from the group consisting of an alcohol, a glycol, an ether, a pyrrolidone compound with five carbon atoms, and combinations thereof to form a solution;
   b) mixing the solution with at least one co-solvent selected from the group consisting of an alcohol, an ether compound with three or more carbon atoms, and combinations thereof, wherein when the organic non-aqueous solvent is an alcohol the co-solvent is not an alcohol, and when the organic non-aqueous solvent is an ether the co-solvent is not an ether compound; and
   c) forming a tablet from the mixture of steps (a) and (b).

2. The method of claim 1 wherein the macrocyclic lactone compound has poor solubility and/or dispersion characteristics in an aqueous environment.

3. The method as claimed in claim 2 wherein the aqueous environment is extracellular fluid.

4. The method as claimed in claim 1 wherein the macrocyclic lactone compound is selected from the group consisting of abamectin and ivermectin.

5. The method as claimed in claim 1 wherein the macrocyclic lactone compound is present in an effective amount sufficient to: reduce growth of parasites; reduce parasite numbers; lower the number of surviving incoming parasite larvae; reduce the number of hypobiotic state parasites; or a combination thereof.

6. The method as claimed in claim 1 wherein the macrocyclic lactone compound is at an effective amount sufficient to provide the animal with a dose of the compound equivalent to that which would be obtained from an oral drench containing the same solubilisable lipophilic compound.

7. The method as claimed in claim 1 wherein the macrocyclic lactone compound is abamectin included at an amount of 0.2 mg to 0.6 mg of abamectin per kg of animal body weight.

8. The method as claimed in claim 1 wherein the macrocyclic lactone compound is ivermectin included at an amount of 0.2 mg to 0.6 mg of ivermectin per kg of animal body weight.

9. The method as claimed in claim 1 wherein the macrocyclic lactone compound is formulated to be rapidly released on oral administration.

10. The method as claimed in claim 1 wherein the macrocyclic lactone compound is formulated so that the compound or compounds remain present in the bloodstream of the animal for at least 24 hours.

11. The method as claimed in claim 1 wherein the macrocyclic lactone compound is formulated so that the compound dissipates from the bloodstream of the animal in a similar manner as an oral drench.

12. The method as claimed in claim 1 wherein the organic solvent is selected from the group consisting of ethyl alcohol; benzyl alcohol; phenethyl alcohol; ethyl benzyl alcohol; glycols; glycol ethers; glycol ether acetates; C1 to C8 alkyl pyrrolidones; and combinations thereof.

13. The method as claimed in claim 1 wherein the organic solvent is benzyl alcohol.

14. The method as claimed in claim 1 wherein the co-solvent is selected from the group consisting of diol alcohols, glycols, aromatic monohydric alcohols, glycol ether acetates, and combinations thereof.

15. The method as claimed in claim 1 wherein the co-solvent is a propylene glycol compound.

16. The method as claimed in claim 1 wherein the co-solvent is monopropylene glycol.

17. A tablet formulated for administration to an animal produced from the method as claimed in claim 1, including at least one macrocyclic lactone compound having anthelmintic activity, at least one organic non-aqueous solvent, and at least one organic co-solvent.

18. The tablet as claimed in claim 17 wherein the tablet remains stable with a less than 10% w/w loss in active concentration during storage for at least 6 months at a temperature of less than 40° C. and relative humidity of less than 75%.

19. The tablet as claimed in claim 17 wherein the tablet remains stable for at least 18 months.

20. The tablet as claimed in claim 17 wherein the tablet is chemically stable whereby the active agent concentration remains at within 10% of initial levels and is physically stable such that no physical alteration is observed in the tablet during storage or at the time of administration.

21. The tablet as claimed in claim 17 wherein the tablet contains mineral sources selected from the group consisting of cobalt, copper, iodine, selenium, zinc and combinations thereof.

22. The tablet as claimed in claim 17 wherein the tablet contains inert compositions selected from the group consisting of binders; fillers; bulking agents; carriers; disintegration agents; glidants; lubricants; and combinations thereof.

23. A tablet formulated for administration to an animal comprising at least one macrocyclic lactone compound having anthelmintic activity, at least one organic non-aqueous solvent selected from the group consisting of an alcohol, a glycol, an ether, a pyrrolidone compound with five carbon atoms, and combinations thereof, and at least one organic co-solvent selected from the group consisting of an alcohol, an ether compound with three or more carbon atoms, and combinations thereof, wherein when the organic non-aqueous solvent is an alcohol the co-solvent is not an alcohol, and when the organic non-aqueous solvent is an ether the co-solvent is not an ether compound, wherein the tablet has a ratio within the range of approximately 1 part macrocyclic lactone compound to 0.8-1.2 parts organic solvent to 3.2-3.6 parts organic co-solvent.

24. A tablet formulated for administration to an animal comprising at least one macrocyclic lactone compound having anthelmintic activity, benzyl alcohol and a propylene glycol compound wherein the tablet has a ratio within the range of approximately 1 part macrocyclic lactone to 0.8-1.2 parts benzyl alcohol to 3.2-3.6 parts propylene glycol compound.

25. A method of treating a non-human animal for parasite infestation by administration of a tablet comprising at least one macrocyclic lactone compound having anthelmintic activity, at least one organic non-aqueous solvent selected from the group consisting of an alcohol, a glycol, an ether, a pyrrolidone compound with five carbon atoms, and combinations thereof, and at least one organic co-solvent selected from the group consisting of an alcohol, an ether compound with three or more carbon atoms, and combinations thereof, and wherein when the organic non-aqueous solvent is an alcohol the co-solvent is not an alcohol, and when the organic non-aqueous solvent is an ether the co-solvent is not an ether compound.

26. The method as claimed in claim 25 wherein the non-human animal is a ruminant animal.

27. The method as claimed in claim 25 wherein the non-human animal is of ovine or bovine species.

28. The method as claimed in claim 25 wherein the parasite infestation is caused by endoparasites.

29. A kit comprising a pill administration device or pill administration composition and one or more tablets as claimed in claim 17.

30. The tablet as claimed in claim 23, wherein the at least one macrocyclic lactone compound having anthelmintic activity is selected from the group consisting of abamectin, levamisole hydrochloride, and albendazole.

31. The tablet as claimed in claim 23, wherein the at least one organic non-aqueous solvent is an alcohol, and the at least one organic co-solvent is a glycol.

* * * * *